(12) United States Patent
McAlister

(10) Patent No.: US 8,926,908 B2
(45) Date of Patent: *Jan. 6, 2015

(54) REACTOR VESSELS WITH PRESSURE AND HEAT TRANSFER FEATURES FOR PRODUCING HYDROGEN-BASED FUELS AND STRUCTURAL ELEMENTS, AND ASSOCIATED SYSTEMS AND METHODS

(71) Applicant: McAlister Technologies, LLC, Phoenix, AZ (US)

(72) Inventor: Roy Edward McAlister, Phoenix, AZ (US)

(73) Assignee: McAlister Technologies, LLC, Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/684,743

(22) Filed: Nov. 26, 2012

(65) Prior Publication Data

US 2013/0309164 A1 Nov. 21, 2013

Related U.S. Application Data

(63) Continuation of application No. 13/027,060, filed on Feb. 14, 2011, now Pat. No. 8,318,100.

(60) Provisional application No. 61/304,403, filed on Feb. 13, 2010.

(51) Int. Cl.
  *B01J 4/00* (2006.01)
  *C10J 3/72* (2006.01)
  (Continued)

(52) U.S. Cl.
  CPC ............... *C10J 3/723* (2013.01); *B01J 19/127* (2013.01); *B01J 19/1812* (2013.01);
  (Continued)

(58) Field of Classification Search
  CPC ........ B01J 19/00; B01J 19/0006; B01J 19/24; B01J 2219/00; B01J 2219/00049; B01J 2219/00051; B01J 2219/00054; B01J 2219/00056; B01J 2219/00058; B01J 2219/00065; B01J 2219/00162; B01J 4/00; B01J 4/008; B01J 4/02; B01J 8/00; B01J 8/0001; B01J 2208/00; B01J 2208/00008; B01J 2208/00017; B01J 2208/00026; B01J 2208/00035; B01J 2208/0007; B01J 2208/00539; B01J 2208/00548; B01J 2208/00557
  USPC .......... 700/301; 422/105, 112, 113, 129, 187, 422/198, 110; 423/644, 648.1; 502/702–704
  See application file for complete search history.

(56) References Cited

U.S. PATENT DOCUMENTS 2,194,092 A 3/1940 Lund et al.
3,613,792 A 10/1971 Hyde et al.
(Continued)

FOREIGN PATENT DOCUMENTS

CA 2521698 A1 8/2005
CH 692927 A5 12/2002
(Continued)

OTHER PUBLICATIONS

"Carnot Thermochemical Cycles." Digital image. Wikipedia, the Free Encyclopedia, Published: Aug. 31, 2010. Accessed: Jan. 4, 2011. Printed: May 20, 2011. <http://en.wikipedia.org/wiki/File:Carnot_thermochemical_cycles.PNG>. p. 1.

(Continued)

*Primary Examiner* — Natasha Young
(74) *Attorney, Agent, or Firm* — Perkins Coie LLP

(57) ABSTRACT

Reactor vessels with pressure and heat transfer features for producing hydrogen-based fuels and structural elements, and associated systems and methods. A representative reactor system includes a first reaction zone and a heat path, a reactant source coupled to the first reaction zone, and a first actuator coupled to cyclically pressurize the first reaction zone. A second reaction zone is in fluid communication with the first, a valve is coupled between the first and second reaction zones to control a flow rate therebetween, and a second actuator is coupled in fluid communication with the second reaction zone to cyclically pressurize the second reaction zone. First and second heat exchangers direct heat from products to reactants in the reaction zones. A controller controls the first and second actuators in a coordinated manner based at least in part on a flow rate of the second product from the second reaction zone.

10 Claims, 3 Drawing Sheets

(51) Int. Cl.
- *B01J 19/12* (2006.01)
- *B01J 19/18* (2006.01)
- *B01J 19/20* (2006.01)
- *C01B 3/24* (2006.01)
- *G01N 35/00* (2006.01)
- *F24J 2/07* (2006.01)
- *C01B 3/26* (2006.01)
- *C10B 53/02* (2006.01)
- *G01M 3/22* (2006.01)
- *B01J 8/00* (2006.01)
- *B01J 19/00* (2006.01)
- *B01J 19/24* (2006.01)
- *G01N 1/40* (2006.01)
- *G01N 1/02* (2006.01)

(52) U.S. Cl.
CPC . *B01J 19/20* (2013.01); *C01B 3/24* (2013.01); *G01N 35/00871* (2013.01); *F24J 2/07* (2013.01); *C01B 3/26* (2013.01); *C10B 53/02* (2013.01); *G01M 3/223* (2013.01); *C10J 3/72* (2013.01); *B01J 2219/00085* (2013.01); *B01J 2219/187* (2013.01); *C01B 2203/0266* (2013.01); *C01B 2203/04* (2013.01); *C01B 2203/0465* (2013.01); *C01B 2203/0485* (2013.01); *C01B 2203/0811* (2013.01); *C01B 2203/0822* (2013.01); *C01B 2203/0872* (2013.01); *C01B 2203/0883* (2013.01); *G01N 1/405* (2013.01); *G01N 35/00613* (2013.01); *G01N 2001/021* (2013.01); *Y02B 10/20* (2013.01); *Y02E 60/366* (2013.01); *Y02E 10/41* (2013.01); *Y02E 60/364* (2013.01); *Y02E 50/14* (2013.01); *Y02E 50/32* (2013.01); *Y02T 10/16* (2013.01)
USPC ........... 422/110; 422/105; 422/112; 422/113; 422/129; 422/187; 422/198

(56) References Cited

U.S. PATENT DOCUMENTS

| | | | |
|---|---|---|---|
| 3,633,372 | A | 1/1972 | Kimmel et al. |
| 3,662,832 | A | 5/1972 | Keeler et al. |
| 3,675,699 | A | 7/1972 | Ocone |
| 3,757,860 | A | 9/1973 | Pritchett |
| 3,788,389 | A | 1/1974 | Waters |
| 3,807,491 | A | 4/1974 | Van Hulsen |
| 3,830,508 | A | 8/1974 | Endicott |
| 3,840,068 | A | 10/1974 | Waters |
| 3,882,937 | A | 5/1975 | Robinson |
| 3,936,652 | A | 2/1976 | Levine |
| 3,975,912 | A | 8/1976 | Greene |
| 3,986,362 | A | 10/1976 | Baciu |
| 3,990,502 | A | 11/1976 | Best |
| 3,991,817 | A | 11/1976 | Clay |
| 4,019,868 | A | 4/1977 | Sebacher et al. |
| 4,053,576 | A | 10/1977 | Fletcher |
| 4,070,861 | A | 1/1978 | Scragg et al. |
| 4,082,865 | A | 4/1978 | Ban et al. |
| 4,099,489 | A | 7/1978 | Bradley |
| 4,138,993 | A | 2/1979 | Conley |
| 4,158,354 | A | 6/1979 | Carden |
| 4,161,211 | A * | 7/1979 | Duffy et al. ............... 165/104.12 |
| 4,169,460 | A | 10/1979 | Popovich et al. |
| 4,172,506 | A | 10/1979 | Terry |
| 4,178,987 | A * | 12/1979 | Bowman et al. ......... 165/104.12 |
| 4,229,184 | A | 10/1980 | Gregg |
| 4,257,239 | A | 3/1981 | Partin et al. |
| 4,343,338 | A | 8/1982 | Hart |
| 4,382,189 | A | 5/1983 | Wilson |
| 4,386,801 | A | 6/1983 | Chapman et al. |
| 4,401,689 | A | 8/1983 | Ban |
| 4,455,045 | A | 6/1984 | Wheeler |
| 4,519,342 | A | 5/1985 | Yoon |
| 4,549,078 | A | 10/1985 | Monahan |
| 4,549,528 | A | 10/1985 | Gibson |
| 4,601,508 | A | 7/1986 | Kerian |
| 4,611,847 | A | 9/1986 | Sullivan |
| 4,620,580 | A | 11/1986 | Groezinger et al. |
| 4,650,651 | A * | 3/1987 | Fuderer .......................... 422/628 |
| 4,704,267 | A | 11/1987 | DiMartino |
| 4,706,651 | A | 11/1987 | Yudow |
| 4,746,160 | A | 5/1988 | Wiesemeyer |
| 4,848,445 | A | 7/1989 | Harper |
| 4,921,580 | A | 5/1990 | Martes et al. |
| 4,978,162 | A | 12/1990 | Labbe |
| 5,058,945 | A | 10/1991 | Elliott, Sr. et al. |
| 5,119,897 | A | 6/1992 | Moriwake |
| 5,132,090 | A | 7/1992 | Volland |
| 5,222,698 | A | 6/1993 | Nelson et al. |
| 5,280,990 | A | 1/1994 | Rinard |
| 5,287,004 | A | 2/1994 | Finley |
| 5,315,868 | A | 5/1994 | Jacobi et al. |
| 5,348,774 | A | 9/1994 | Golecki et al. |
| 5,407,245 | A | 4/1995 | Geropp |
| 5,442,934 | A | 8/1995 | Wolflick |
| 5,498,059 | A | 3/1996 | Switlik |
| 5,558,721 | A | 9/1996 | Kohmura et al. |
| 5,560,443 | A | 10/1996 | DuBose |
| 5,618,134 | A | 4/1997 | Balch |
| 5,647,877 | A * | 7/1997 | Epstein ........................... 48/210 |
| 5,844,324 | A | 12/1998 | Spriggle |
| 5,881,559 | A | 3/1999 | Kawamura |
| 5,882,382 | A | 3/1999 | Hachisuka et al. |
| 5,986,429 | A | 11/1999 | Mula, Jr. |
| 6,012,065 | A | 1/2000 | Boucher et al. |
| 6,068,328 | A | 5/2000 | Gazdzinski |
| 6,074,696 | A | 6/2000 | Sato |
| 6,081,183 | A | 6/2000 | Mading et al. |
| 6,089,224 | A | 7/2000 | Poulek |
| 6,092,861 | A | 7/2000 | Whelan |
| 6,155,212 | A | 12/2000 | McAlister |
| 6,200,069 | B1 | 3/2001 | Miller |
| 6,216,599 | B1 | 4/2001 | Cavanagh |
| 6,220,193 | B1 | 4/2001 | Dilks |
| 6,309,010 | B1 | 10/2001 | Whitten |
| 6,334,928 | B1 | 1/2002 | Sekine et al. |
| 6,378,932 | B1 | 4/2002 | Fasel et al. |
| 6,409,252 | B1 | 6/2002 | Andrus |
| 6,464,755 | B2 | 10/2002 | Nakanishi et al. |
| 6,502,533 | B1 | 1/2003 | Meacham |
| 6,508,209 | B1 | 1/2003 | Collier, Jr. |
| 6,531,704 | B2 | 3/2003 | Yadav et al. |
| 6,534,210 | B2 | 3/2003 | Luken et al. |
| 6,571,747 | B1 | 6/2003 | Gerstweiler |
| 6,585,785 | B1 | 7/2003 | Warren et al. |
| 6,630,267 | B2 | 10/2003 | Badding et al. |
| 6,749,043 | B2 | 6/2004 | Brown et al. |
| 6,756,140 | B1 | 6/2004 | McAlister |
| 6,756,565 | B2 | 6/2004 | Suenaga et al. |
| 6,838,782 | B2 | 1/2005 | Vu |
| 6,854,788 | B1 | 2/2005 | Graham |
| 6,881,508 | B2 | 4/2005 | Penev |
| 6,886,249 | B2 | 5/2005 | Smalc |
| 6,889,755 | B2 | 5/2005 | Zuo et al. |
| 6,897,575 | B1 | 5/2005 | Yu |
| 6,908,297 | B2 | 6/2005 | Dafft et al. |
| 6,919,062 | B1 | 7/2005 | Vasileiadis et al. |
| 6,923,004 | B2 | 8/2005 | Chandran et al. |
| 6,926,345 | B2 | 8/2005 | Ortega et al. |
| 6,979,049 | B2 | 12/2005 | Ortega et al. |
| 6,984,305 | B2 | 1/2006 | McAlister |
| 7,014,737 | B2 | 3/2006 | Harutyunyan et al. |
| 7,033,570 | B2 | 4/2006 | Weimer et al. |
| 7,051,794 | B2 | 5/2006 | Luo |
| 7,140,181 | B1 | 11/2006 | Jensen et al. |
| 7,152,908 | B2 | 12/2006 | Shahbazi |
| 7,165,804 | B2 | 1/2007 | Shahbazi |
| 7,179,383 | B1 | 2/2007 | Porter et al. |
| 7,185,944 | B2 | 3/2007 | Shahbazi |
| 7,207,620 | B2 | 4/2007 | Cosgrove et al. |

(56) References Cited

U.S. PATENT DOCUMENTS

| | | |
|---|---|---|
| 7,210,467 B2 | 5/2007 | Kweon et al. |
| 7,211,905 B1 | 5/2007 | McDavid, Jr. |
| 7,237,827 B2 | 7/2007 | Shahbazi |
| 7,243,980 B2 | 7/2007 | Vala |
| 7,250,151 B2 | 7/2007 | Tonkovich et al. |
| 7,285,350 B2 | 10/2007 | Keefer et al. |
| 7,293,533 B2 | 11/2007 | Hemsath |
| 7,306,781 B2 | 12/2007 | Retallick et al. |
| 7,337,612 B2 | 3/2008 | Skinnes et al. |
| 7,343,971 B2 | 3/2008 | Pfefferle |
| 7,397,141 B2 | 7/2008 | Gouker |
| 7,420,004 B2 | 9/2008 | Hardy et al. |
| 7,426,959 B2 | 9/2008 | Wang et al. |
| 7,449,158 B2 | 11/2008 | Haueter et al. |
| 7,484,553 B2 | 2/2009 | Lai et al. |
| 7,504,739 B2 | 3/2009 | Enis et al. |
| 7,527,094 B2 | 5/2009 | McKinzie et al. |
| 7,568,479 B2 | 8/2009 | Rabinowitz |
| 7,582,167 B2 | 9/2009 | Kaszuba et al. |
| 7,585,339 B2 | 9/2009 | Dahl et al. |
| 7,587,998 B2 | 9/2009 | Hotta et al. |
| 7,597,068 B2 | 10/2009 | Arai et al. |
| 7,608,120 B2 | 10/2009 | Wunning |
| 7,621,262 B2 | 11/2009 | Zubeck |
| 7,628,137 B1 | 12/2009 | McAlister |
| 7,692,170 B2 | 4/2010 | Gaus et al. |
| 7,695,709 B2 | 4/2010 | Miki et al. |
| 7,713,642 B2 | 5/2010 | Warner et al. |
| 7,714,258 B2 | 5/2010 | Dalton |
| 7,753,122 B2 | 7/2010 | Curlett |
| 7,775,261 B2 | 8/2010 | Valenzuela |
| 7,788,924 B2 | 9/2010 | Hines |
| 7,789,182 B2 | 9/2010 | Bradley et al. |
| 7,799,315 B2 | 9/2010 | Amendola |
| 7,808,121 B1 | 10/2010 | Glynn |
| 7,856,843 B2 | 12/2010 | Enis et al. |
| 7,884,308 B1 | 2/2011 | Mejia |
| 7,943,045 B2 | 5/2011 | Rohrich et al. |
| 7,955,478 B2 | 6/2011 | McClure |
| 7,963,328 B2 | 6/2011 | Khinkis et al. |
| 7,971,861 B2 | 7/2011 | Soininen |
| 7,972,471 B2 | 7/2011 | Sant |
| 8,043,592 B2 | 10/2011 | Krass |
| 8,053,916 B2 | 11/2011 | Edwards et al. |
| 8,083,520 B2 | 12/2011 | Mueller et al. |
| 8,136,740 B2 | 3/2012 | Hagen et al. |
| 8,202,817 B2 | 6/2012 | Yuge et al. |
| 8,220,539 B2 | 7/2012 | Vinegar et al. |
| 8,449,634 B2 * | 5/2013 | Tamura et al. ............ 48/197 R |
| 2002/0102188 A1 | 8/2002 | Hsu et al. |
| 2003/0008183 A1 | 1/2003 | Hsu |
| 2003/0178195 A1 | 9/2003 | Agee et al. |
| 2004/0200618 A1 | 10/2004 | Piekenbrock |
| 2004/0219737 A1 | 11/2004 | Quon |
| 2004/0247957 A1 | 12/2004 | Hatano et al. |
| 2004/0253168 A1 | 12/2004 | Chu |
| 2004/0265448 A1 | 12/2004 | Shiau et al. |
| 2004/0266615 A1 | 12/2004 | Watson et al. |
| 2005/0029120 A1 | 2/2005 | Bar-Gadda |
| 2005/0061486 A1 | 3/2005 | Yang |
| 2005/0079977 A1 | 4/2005 | Choi et al. |
| 2005/0265919 A1 | 12/2005 | Lomax et al. |
| 2005/0272856 A1 | 12/2005 | Cooper et al. |
| 2006/0005738 A1 | 1/2006 | Kumar |
| 2006/0005739 A1 | 1/2006 | Kumar |
| 2006/0048808 A1 | 3/2006 | Ruckman et al. |
| 2006/0266043 A1 | 11/2006 | Jerome |
| 2007/0031718 A1 | 2/2007 | Fujimura et al. |
| 2007/0065686 A1 | 3/2007 | Fan et al. |
| 2007/0138006 A1 | 6/2007 | Oakes et al. |
| 2007/0191664 A1 * | 8/2007 | Hershkowitz et al. ........ 585/539 |
| 2007/0199339 A1 | 8/2007 | Ishihara et al. |
| 2007/0205298 A1 | 9/2007 | Harrison et al. |
| 2007/0220810 A1 | 9/2007 | Leveson et al. |
| 2007/0295477 A1 | 12/2007 | Mueller et al. |
| 2008/0073066 A1 | 3/2008 | Chang et al. |
| 2008/0086946 A1 | 4/2008 | Weimer et al. |
| 2008/0098654 A1 | 5/2008 | Cherry et al. |
| 2008/0170975 A1 | 7/2008 | Ahn et al. |
| 2008/0175766 A1 | 7/2008 | Mankins et al. |
| 2008/0241033 A1 | 10/2008 | Nazri |
| 2008/0295883 A1 | 12/2008 | Ducellier et al. |
| 2009/0062591 A1 | 3/2009 | Bingue et al. |
| 2009/0206666 A1 | 8/2009 | Sella et al. |
| 2009/0258278 A1 | 10/2009 | Steinberg |
| 2009/0313886 A1 | 12/2009 | Hinman et al. |
| 2010/0000874 A1 | 1/2010 | Hinman et al. |
| 2010/0043404 A1 | 2/2010 | Hebbale et al. |
| 2010/0107994 A1 | 5/2010 | Moriarty et al. |
| 2010/0140950 A1 | 6/2010 | Pitre |
| 2010/0174124 A1 | 7/2010 | Tonkovich et al. |
| 2010/0242352 A1 | 9/2010 | Perkins et al. |
| 2011/0061295 A1 | 3/2011 | McAlister |
| 2011/0061383 A1 | 3/2011 | McAlister |
| 2011/0100731 A1 | 5/2011 | Hassan |
| 2011/0197599 A1 | 8/2011 | Stewart et al. |
| 2011/0214986 A1 | 9/2011 | Brown |
| 2011/0220040 A1 | 9/2011 | McAlister |
| 2011/0284298 A1 | 11/2011 | Ajisaka |
| 2011/0315539 A1 | 12/2011 | Zadik et al. |
| 2012/0009119 A1 | 1/2012 | Yampolsky |
| 2012/0118878 A1 | 5/2012 | Kim et al. |
| 2012/0119510 A1 | 5/2012 | Herzen et al. |

FOREIGN PATENT DOCUMENTS

| | | |
|---|---|---|
| CN | 101042261 A | 9/2007 |
| CN | 101091900 A | 12/2007 |
| CN | 101597025 A | 12/2009 |
| EA | 200702287 A1 | 4/2008 |
| EP | 1394103 A1 | 3/2004 |
| EP | 1658892 A1 | 5/2006 |
| FR | 2923731 A1 | 5/2009 |
| GB | 24256 | 7/1911 |
| JP | 59046375 | 3/1984 |
| JP | S62203328 A | 9/1987 |
| JP | 01215701 | 8/1989 |
| JP | H02025571 | 1/1990 |
| JP | H04044314 | 2/1992 |
| JP | H0637348 | 5/1994 |
| JP | 0725637 | 3/1995 |
| JP | 0940491 | 2/1997 |
| JP | 09055374 | 2/1997 |
| JP | 10172960 | 6/1998 |
| JP | H11108465 A | 4/1999 |
| JP | 2000271472 A | 10/2000 |
| JP | 2000353690 A | 12/2000 |
| JP | 2001080902 A | 3/2001 |
| JP | 2001181846 A | 7/2001 |
| JP | 2001262353 A | 9/2001 |
| JP | 03215670 B2 | 10/2001 |
| JP | 2002158175 A | 5/2002 |
| JP | 2003040601 A | 2/2003 |
| JP | 2003166059 A | 6/2003 |
| JP | 2005511467 A | 6/2003 |
| JP | 2005021876 A | 1/2005 |
| JP | 2005213069 A | 8/2005 |
| JP | 2007139399 A | 6/2007 |
| JP | 2007150012 A | 6/2007 |
| JP | 2007208076 A | 8/2007 |
| JP | 2007527348 A | 9/2007 |
| JP | 2007254180 A | 10/2007 |
| JP | 2008503709 A | 2/2008 |
| JP | 2009010263 A | 1/2009 |
| JP | 2009500274 A | 1/2009 |
| JP | 2009513466 A | 4/2009 |
| JP | 2010003568 A | 1/2010 |
| JP | 2010006653 A | 1/2010 |
| JP | 2010025031 A | 2/2010 |
| JP | 2011507218 A | 3/2011 |
| KR | 100794943 B1 | 1/2008 |
| KR | 20120077307 A | 7/2012 |
| RU | 2011864 C1 | 4/1994 |
| RU | 2120913 C1 | 10/1998 |

(56) References Cited

FOREIGN PATENT DOCUMENTS

| | | | |
|---|---|---|---|
| RU | 2312059 C1 | 12/2007 | |
| RU | 2403379 C1 | 11/2010 | |
| SU | 1498908 A1 | 8/1989 | |
| SU | 1776298 | 11/1992 | |
| WO | WO-2007053370 A2 | 5/2007 | |
| WO | WO-2007140441 A2 | 12/2007 | |
| WO | WO 2008/035776 A1 * | 3/2008 | |
| WO | WO-2008031488 A1 | 3/2008 | |
| WO | WO-2008076840 A2 | 6/2008 | |
| WO | WO-2008093661 A1 | 8/2008 | |
| WO | WO-2009098375 A1 | 8/2009 | |
| WO | WO-2010097890 A1 | 9/2010 | |
| WO | WO-2011154945 A2 | 12/2011 | |
| WO | WO-2012014197 A1 | 2/2012 | |

OTHER PUBLICATIONS

"Closed Loop Thermochemical Energy Storage System Using Ammonia." Australian National University College of Engineering & Computer Science—Solar Thermal Group. Accessed: Jan. 4, 2011. Printed: May 20, 2011. <http://solar-thermal.anu.edu.au/high-temperature/thermochemical-energy-storage/>. pp. 1-2.

"SI Cycle." Digital image. Sandia National Laboratories: Energy, Resources and Nonproliferation. Accessed: Jan. 4, 2011. Printed: Jun. 13, 2011. <http://www.sandia.gov/ERN/images/SI-cycle2.jpg>. p. 1.

"Solar Hydrogen." Digital image. Swiss Federal Institute of Technology, Department of Mechanical and Process Engineering, Zurich. Accessed: Jan. 4, 2011. Printed: May 23, 2011. p. 1. <http://www.pre.ethz.ch/research/projects/imgs/solarhydro_1.jpg>.

"The Carbon Cycle : Feature Articles." NASA Earth Observatory : Home. Web. Accessed: Jul. 1, 2010. Printed: Jun. 13, 2011. 12 pages. <http://earthobservatory.nasa.gov/Features/CarbonCycle>.

"The Solar Zinc Route." Digital image. Swiss Federal Institute of Technology, Department of Mechanical and Process Engineering, Zurich. Accessed: Jan. 4, 2011. Printed: May 20, 2011. <http://www.pre.ethz.ch/research/projects/imgs/solzinc_1.jpg>. p. 1.

"Zinc Zinc-oxide Thermochemical Cycle." Digital image. Wikipedia, the Free Encyclopedia, Published: Dec. 21, 2008. Accessed: Jan. 4, 2011. Printed: May 20, 2011. <http://en.wikipedia.org/wiki/File:Zinc_zinc-oxide_thermochemical_cycle.jpg>. p. 1.

Chen et al. "Parylene-Encapsulated Copolymeric Membranes as Localized and Sustained Drug Delivery Platforms." Annals of Biomedical Engineering, vol. 37, Issue 10 (Oct. 2009): pp. 2003-2017.

Chen et al. "Thermochemistry Concept Map." Teacherknowledge Wikispace, Published: Nov. 20, 2006. <http://teacherknowledge.wikispaces.com/file/view/Thermochemistry+concept+map+-+Extended.pdf>. p. 1.

Elias et al., "Control of Graphene's Properties by Reversible Hydrogenation: Evidence for Graphene", Science, vol. 23, 2009, pp. 610-613.

Food and Agriculture Organization of the United Nations. "Carbon Sequestration Options under the Clean Development Mechanism to Address Land Degradation." World Soil Resources Reports. Rome, 2000. pp. 1-45.

Foust et al. "An Economic and Environmental Comparison of a Biochemical and a Thermochemical Lignocellulosic Ethanol Conversion Processes." Cellulose, vol. 16, Issue 4. Jun. 10, 2009. pp. 547-565.

Funk, James E. "Thermochemical Processes for the Production of Hydrogen from Water." College of Engineering, University of Kentucky, Lexington, Kentucky. 1975. pp. 1-9.

Hackett et al. "Evaluation of Conversion Technoloigy Processes and Products: Appendix A—Discussion of Thermochemical Process Definitions." University of California, Davis. Sep. 2004. pp. 1-7.

Kasting, James F. "The Carbon Cycle, Climate, and the Long-Term Effects of Fossil Fuel Burning." U.S. Global Change Research Information Office. 1998. Web. Accessed: Jul. 1, 2010. Printed: Jun. 13, 2011. <http://www.gcrio.org/CONSEQUENCES/vol4no1/carbcycle.html>.

U.S. Energy Information Administration."Greenhouse Gases—Energy Explained, Your Guide to Understanding Energy." Web. Accessed: Jul. 1, 2010. Printed: Jun. 13, 2011. 1 Pages. <http://www.eia.gov/energyexplained/index.cfm?page=environment_about_ghg>.

US Environmental Protection Agency. "Cap and Trade." Web. Accessed: Jul. 1, 2010. Printed: Jun. 13, 2011. <http://www.epa.gov/captrade/>.

US Environmental Protection Agency. "Carbon Dioxide—Geologic Sequestration | Climate Change—Greenhouse Gas Emissions | U.S. EPA." Web. Accessed: Jul. 1, 2010. Printed: Jun. 13, 2011. <http://www.epa.gov/climatechange/emissions/co2_geosequest.html>.

US Environmental Protection Agency. "Carbon Dioxide | Climate Change—Greenhouse Gas Emissions | U.S. EPA". Web. Accessed: Jul. 1, 2010. Printed: Jun. 13, 2011. 1 Page. <http://www.epa.gov/climatechange/emissions/co2.html>.

US Environmental Protection Agency. "EPA Preliminary Analysis of the Waxman-Markey Discussion Draft". Web. Accessed: Jul. 1, 2010. Printed: Jun. 13, 2011. <http://www.epa.gov/climatechange/economics/pdfs/WM-Analysis.pdf>.

Solar Collectors, Energy Storage, and Materials, pp. 443-444 (DeWinter, Francis, 1991).

Wikipedia > Aerogel > Carbon—"Carbon aerogels are also extremely 'black' in the infrared spectrum, reflecting only 0.3% of radiation between 250 nm and 14.3 μm, making them efficient for solar energy collectors," 1 page.

Vegners, Raimonds Maris; "Collodial Carbon and Silica : Their Use in Solar Energy" Table of Contents and Introduction of Thesis, University of Sydney, Feb. 1985, 5 pages.

N. Muradov: "Catalysis of Methane decomposition over elemental carbon", Catalysis Communications, No. 3-4, Jul. 1, 2001, pp. 89-94, p. 89, right-hand column, paragraph 2.

Muradov et al: "Catalytic Dissociation of Hydrocarbons: a Route to CO2-free Hydrogen", 15th Annual Symposium on Catalysis in Petroleum Refining & Petrochemicals.

Supplemental European Search Report; Application EP 11742969.6 Dated May 9, 2014; pp. 6.

* cited by examiner

REACTOR VESSELS WITH PRESSURE AND HEAT TRANSFER FEATURES FOR PRODUCING HYDROGEN-BASED FUELS AND STRUCTURAL ELEMENTS, AND ASSOCIATED SYSTEMS AND METHODS

CROSS-REFERENCE TO RELATED APPLICATIONS

The present application claims priority to and the benefit of U.S. Patent Application No. 61/304,403, filed on Feb. 13, 2010 and titled FULL SPECTRUM ENERGY AND RESOURCE INDEPENDENCE, which is incorporated herein by reference in its entirety. To the extent the foregoing application and/or any other materials incorporated herein by reference conflict with the disclosure presented herein, the disclosure herein controls.

TECHNICAL FIELD

The present technology relates generally to chemical reactor vessels with pressure and heat transfer features for producing hydrogen-based fuels and structural elements, and associated systems and methods. In particular embodiments, such reactor vessels can be used to produce clean-burning, hydrogen-based fuels from a wide variety of feedstocks, and can produce structural building blocks from carbon and/or other elements that are released when forming the hydrogen-based fuels.

BACKGROUND

Renewable energy sources such as solar, wind, wave, falling water, and biomass-based sources have tremendous potential as significant energy sources, but currently suffer from a variety of problems that prohibit widespread adoption. For example, using renewable energy sources in the production of electricity is dependent on the availability of the sources, which can be intermittent. Solar energy is limited by the sun's availability (i.e., daytime only), wind energy is limited by the variability of wind, falling water energy is limited by droughts, and biomass energy is limited by seasonal variances, among other things. As a result of these and other factors, much of the energy from renewable sources, captured or not captured, tends to be wasted.

The foregoing inefficiencies associated with capturing and saving energy limit the growth of renewable energy sources into viable energy providers for many regions of the world, because they often lead to high costs of producing energy. Thus, the world continues to rely on oil and other fossil fuels as major energy sources because, at least in part, government subsidies and other programs supporting technology developments associated with fossil fuels make it deceptively convenient and seemingly inexpensive to use such fuels. At the same time, the replacement cost for the expended resources, and the costs of environment degradation, health impacts, and other by-products of fossil fuel use are not included in the purchase price of the energy resulting from these fuels.

In light of the foregoing and other drawbacks currently associated with sustainably producing renewable resources, there remains a need for improving the efficiencies and commercial viabilities of producing products and fuels with such resources.

DETAILED DESCRIPTION

1. Overview

Figure 1:
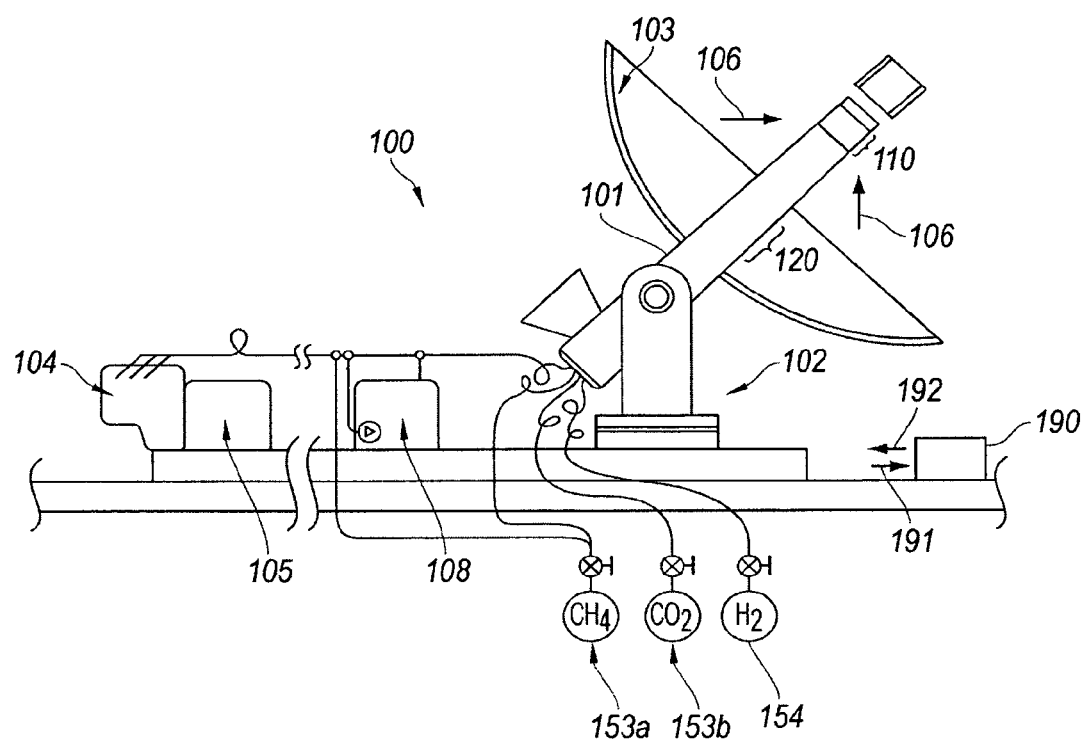
FIG. 1 is a partially schematic, partially cross-sectional illustration of a solar-heated reactor vessel configured in accordance with an embodiment of the present technology.

Several examples of devices, systems and methods for conducting interconnected exothermic and endothermic reactions in a chemical reactor are described below. The interconnections can be based on pressure differences and/or temperature differences between regions and constituents within the reactor. Such reactors can be used to produce hydrogen fuels and/or other useful end products. Accordingly, the reactors can produce clean-burning fuel and can re-purpose carbon and/or other constituents for use in durable goods, including polymers and carbon composites. Although the following description provides many specific details of the following examples in a manner sufficient to enable a person skilled in the relevant art to practice, make and use them, several of the details and advantages described below may not be necessary to practice certain examples of the technology. Additionally, the technology may include other examples that are within the scope of the claims but are not described here in detail.

References throughout this specification to "one example," "an example," "one embodiment" or "an embodiment" mean that a particular feature, structure, process or characteristic described in connection with the example is included in at least one example of the present technology. Thus, the occurrences of the phrases "in one example," "in an example," "one embodiment" or "an embodiment" in various places throughout this specification are not necessarily all referring to the same example. Furthermore, the particular features, structures, routines, steps or characteristics may be combined in any suitable manner in one or more examples of the technology. The headings provided herein are for convenience only and are not intended to limit or interpret the scope or meaning of the claimed technology.

Certain embodiments of the technology described below may take the form of computer-executable instructions, including routines executed by a programmable computer or controller. Those skilled in the relevant art will appreciate that the technology can be practiced on computer or controller systems other than those shown and described below. The technology can be embodied in a special-purpose computer, controller, or data processor that is specifically programmed, configured or constructed to perform one or more of the computer-executable instructions described below. Accordingly, the terms "computer" and "controller" as generally used herein refer to any data processor and can include internet appliances, hand-held devices, multi-processor systems, programmable consumer electronics, network computers, mini-computers, and the like. The technology can also be practiced in distributed environments where tasks or modules are performed by remote processing devices that are linked through a communications network. Aspects of the technology described below may be stored or distributed on computer-readable media, including magnetic or optically readable or removable computer discs as well as media distributed electronically over networks. In particular embodiments, data structures and transmissions of data particular to aspects of the technology are also encompassed within the scope of the present technology. The present technology encompasses both methods of programming computer-readable media to perform particular steps, as well as executing the steps.

2. Representative Reactors and Associated Methodologies

FIG. 1 is a partially schematic, partially cross-sectional illustration of a system 100 configured to conduct interactive endothermic and exothermic chemical reactions in accordance with an embodiment of the present technology. The system 100 can include a reactor vessel 101 having multiple reaction zones, shown in FIG. 1 as a first reaction zone 110 and a second reaction zone 120. The system 100 includes features for providing energy to both reaction zones, for example, a suitable heat source, such as a solar concentrator 103 positioned to direct solar energy 106 into the first reaction zone 110. In this embodiment, the reactor vessel 101 and the solar concentrator 103 are mounted to a pedestal 102 that can move with multiple degrees of freedom (e.g. rotate about two orthogonal axes) to position the solar concentrator 103 to capture solar energy throughout the course of the day.

The system 100 can further include supplies of reactants and other chemical constituents, including a methane supply 153a, a carbon dioxide supply 153b, and a hydrogen supply 154. In a particular embodiment, the methane and carbon dioxide are provided to the reactor vessel 101 to produce methanol. The methanol represents a denser and/or more versatile hydrogen carrier that has increased utility for vehicle and other fuel storage and transport purposes. The hydrogen can be stored at a hydrogen storage tank 108. As will be described in further detail below, the hydrogen can be used to pressurize the second reaction zone 120, and/or provide power to an engine 104 and generator 105. The generator 105 can provide power for the overall system 100. In other embodiments, the engine 104 and/or generator 105 can be located far away from the rest of the system 100 and can provide power to devices other than the system 100. In such cases, the hydrogen can be supplied to the engine 104 via a pipeline or other transport device. The system 100 can further include features that allow the reactions at the first and second reaction zones 110, 120 to continue in the absence of sufficient solar energy (e.g. at night). Further details are described below with reference to FIG. 2. The system 100 can also include a controller 190 that receives input signals 191 from any of a variety of sensors, transducers, and/or other elements of the system 100, and, in response to information received from these elements, delivers control signals 192 to adjust operational parameters of the system 100. Further details of representative closed-loop control arrangements are also described further below with reference to FIGS. 2 and 3.

Figure 2:
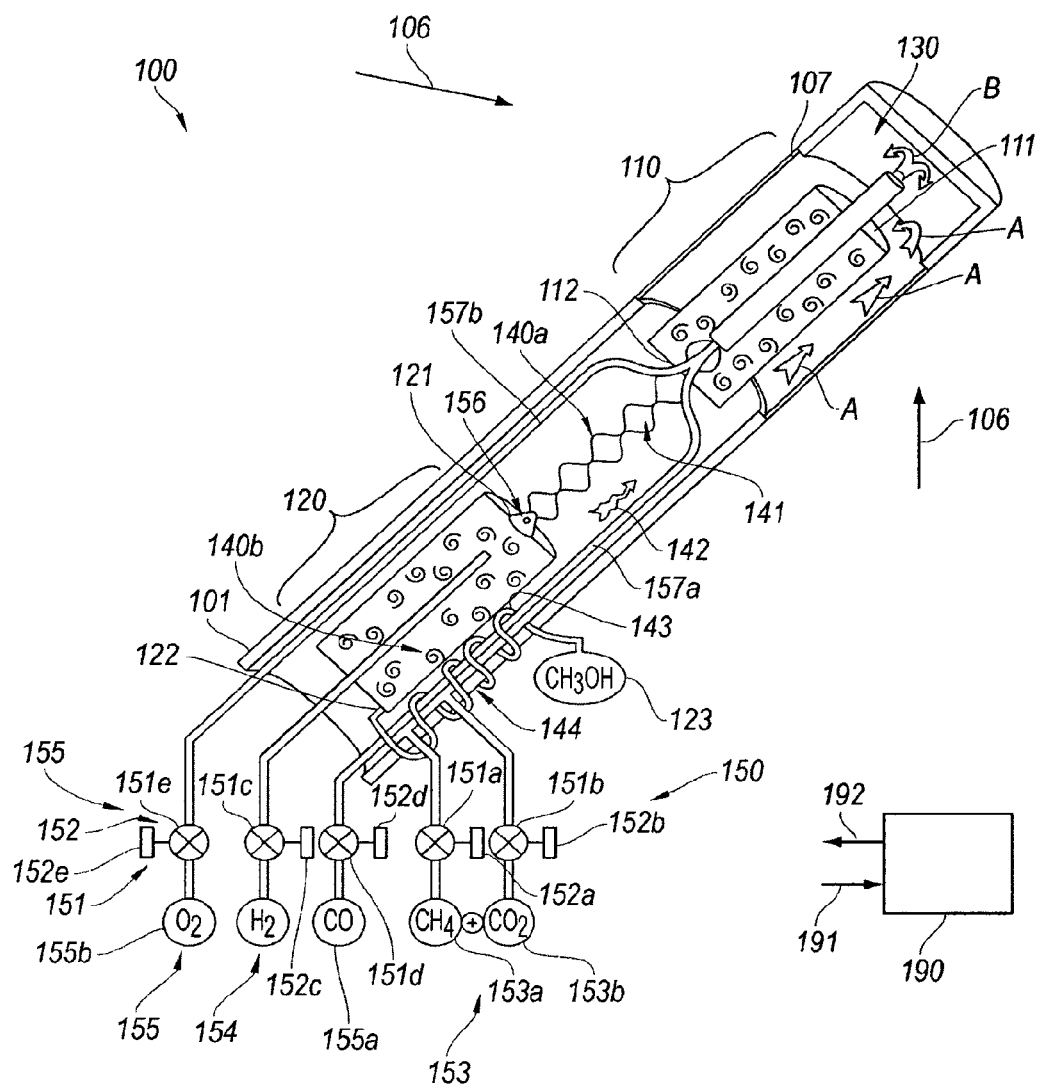
FIG. 2 is a partially schematic, cross-sectional illustration of a reactor having interacting endothermic and exothermic reaction zones in accordance with an embodiment of the disclosure.

FIG. 2 is a partially schematic, cross-sectional illustration of particular components of the system 100, including the reactor vessel 101. The reactor vessel 101 includes the first reaction zone 110 positioned toward the upper left of FIG. 2 (e.g., at a first reactor portion) to receive incident solar radiation 106, e.g., through a solar transmissive surface 107. The second reaction zone 120 is also positioned within the reactor vessel 101, e.g., at a second reactor portion, to receive products from the first reaction zone 110 and to produce an end product, for example, methanol. Reactant sources 153 provide reactants to the reactor vessel 101, and a product collector 123 collects the resulting end product. A regulation system 150, which can include valves 151 or other regulators and corresponding actuators 152, is coupled to the reactant sources 153 to control the delivery of reactants to the first reaction zone 110 and to control other flows within the system 100. In other embodiments, the valves can be replaced by or supplemented with other mechanisms, e.g., pumps.

In a particular embodiment, the reactant sources 153 include a methane source 153a and a carbon dioxide source 153b. The methane source 153a is coupled to a first reactant valve 151a having a corresponding actuator 152a, and the carbon dioxide source 153b is coupled to a second reactant valve 151b having a corresponding actuator 152b. The reactants pass into the reaction vessel 101 and are conducted upwardly around the second reaction zone 120 and the first reaction zone 110 as indicated by arrows A. As the reactants travel through the reactor vessel 101, they can receive heat from the first and second reaction zones 110, 120 and from products passing from the first reaction zone 110 to the second reaction zone 120, as will be described in further detail later. The reactants enter the first reaction zone 110 at a first reactant port 111. At the first reaction zone 110, the reactants can undergo the following reaction:

$$CH_4 + CO_2 + HEAT \rightarrow 2CO + 2H_2 \qquad \text{[Equation 1]}$$

In a particular embodiment, the foregoing endothermic reaction is conducted at about 900° C. and at pressures of up to about 1,500 psi. In other embodiments, reactions with other reactants can be conducted at other temperatures at the first reaction zone 110. The first reaction zone 110 can include any of a variety of suitable catalysts, for example, a nickel/aluminum oxide catalyst. In particular embodiments, the reactants and/or the first reaction zone 110 can be subjected to acoustic pressure fluctuation (in addition to the overall pressure changes caused by introducing reactants, undergoing the reaction, and removing products from the first reaction zone 110) to aid in delivering the reactants to the reaction sites of the catalyst. In any of these embodiments, the products produced at the first reaction zone 110 (e.g. carbon monoxide and hydrogen) exit the first reaction zone 110 at a first product port 112 and enter a first heat exchanger 140a. The first products travel through the first heat exchanger 140a along a first flow path 141 and transfer heat to the incoming reactants traveling along a second flow path 142. Accordingly, the incoming reactants can be preheated at the first heat exchanger 140a, and by virtue of passing along or around the outside of the first reaction zone 110. In particular embodiments, one or more surfaces of the first heat exchanger 140a can include elements or materials that absorb radiation at one frequency and re-radiate it at another. Further details of suitable materials and arrangements are disclosed in co-pending U.S. application Ser. No. 13/027,015 titled "CHEMICAL REACTORS WITH RE-RADIATING SURFACES AND ASSOCIATED SYSTEMS AND METHODS", filed concurrently herewith and incorporated herein by reference.

The first products enter the second reaction zone 120 via a second reactant port 121 and a check valve 156 or other flow inhibitor. The check valve 156 is configured to allow a one-way flow of the first products into the second reaction zone 120 when the pressure of the first products exceeds the pressure in the second reaction zone 120. In other embodiments, the check valve 156 can be replaced with another mechanism, e.g., a piston or pump that conveys the first products to the second reaction zone 120.

At the second reaction zone 120, the first products from the first reaction zone 110 undergo an exothermic reaction, for example:

$$2CO + 2H_2 + 2'H_2 \rightarrow CH_3OH + HEAT \qquad \text{[Equation 2]}$$

The foregoing exothermic reaction can be conducted at a temperature of approximately 250° C. and in many cases at a pressure higher than that of the endothermic reaction in the first reaction zone 110. To increase the pressure at the second reaction zone 120, the system 100 can include an additional constituent source 154 (e.g. a source of hydrogen) that is provided to the second reaction zone 120 via a valve 151c and corresponding actuator 152c. The additional constituent (e.g. hydrogen, represented by 2'H$_2$ in Equation 2) can pressurize the second reaction zone with or without necessarily participating as a consumable in the reaction identified in Equation 2. In particular, the additional hydrogen may be produced at pressure levels beyond 1,500 psi, e.g., up to about 5,000 psi or more, to provide the increased pressure at the second reaction zone 120. In a representative embodiment, the additional hydrogen may be provided in a separate dissociation reaction using methane or another reactant. For example, the hydrogen can be produced in a separate endothermic reaction, independent of the reactions at the first and second reaction zones 110, 120, as follows:

$$CH_4 + HEAT \rightarrow C + 2H_2 \qquad [\text{Equation 3}]$$

In addition to producing hydrogen for pressurizing the second reaction zone 120, the foregoing reaction can produce carbon suitable to serve as a building block in the production of any of a variety of suitable end products, including polymers, self-organizing carbon-based structures such as graphene, carbon composites, and/or other materials. Further examples of suitable products are included in co-pending U.S. application Ser. No. 13/027,214 titled "ARCHITECTURAL CONSTRUCT HAVING FOR EXAMPLE A PLURALITY OF ARCHITECTURAL CRYSTALS" filed Feb. 14, 2011 and incorporated herein by reference.

The reaction at the second reaction zone 120 can be facilitated with a suitable catalyst, for example, copper, zinc, aluminum and/or compounds including one or more of the foregoing elements. The product resulting from the reaction at the second reaction zone 120 (e.g. methanol) is collected at the product collector 123. Accordingly, the methanol exits the second reaction zone 120 at a second product port 122 and passes through a second heat exchanger 140b. At the second heat exchanger 140b, the methanol travels along a third flow path 143 and transfers heat to the incoming constituents provided to the first reaction zone 110 along a fourth flow path 144. Accordingly, the two heat exchangers 140a, 140b can increase the overall efficiency of the reactions taking place in the reactor vessel 101 by conserving and recycling the heat generated at the first and second reaction zones.

In a particular embodiment, energy is provided to the first reaction zone 110 via the solar concentrator 103 described above with reference to FIG. 2. Accordingly, the energy provided to the first reaction zone 110 by the solar collector 103 will be intermittent. The system 100 can include a supplemental energy source that allows the reactions to continue in the absence of sufficient solar energy. In particular, the system 100 can include a supplemental heat source 155. For example, the supplemental heat source 155 can include a combustion reactant source 155a (e.g. providing carbon monoxide) and an oxidizer source 155b (e.g. providing oxygen). The flows from the reactant source 155a and oxidizer source 155b are controlled by corresponding valves 151d, 151e, and actuators 152d, 152e. In operation, the reactant and oxidizer are delivered to the reactor vessel 101 via corresponding conduits 157a, 157b. The reactant and oxidizer can be preheated within the reactor vessel 101, before reaching a combustion zone 130, as indicated by arrow B. At the combustion zone 130, the combustion reactant and oxidizer are combusted to provide heat to the first reaction zone 110, thus supporting the endothermic reaction taking place within the first reaction zone 110 in the absence of sufficient solar energy. The result of the combustion can also yield carbon dioxide, thus reducing the need for carbon dioxide from the carbon dioxide source 153b. The controller 190 can control when the secondary heat source 155 is activated and deactivated, e.g., in response to a heat or light sensor.

In another embodiment, the oxygen provided by the oxidizer source 155b can react directly with the methane at the combustion zone 130 to produce carbon dioxide and hydrogen. This in turn can also reduce the amount of carbon dioxide required at the first reaction zone 110.

Figure 3:
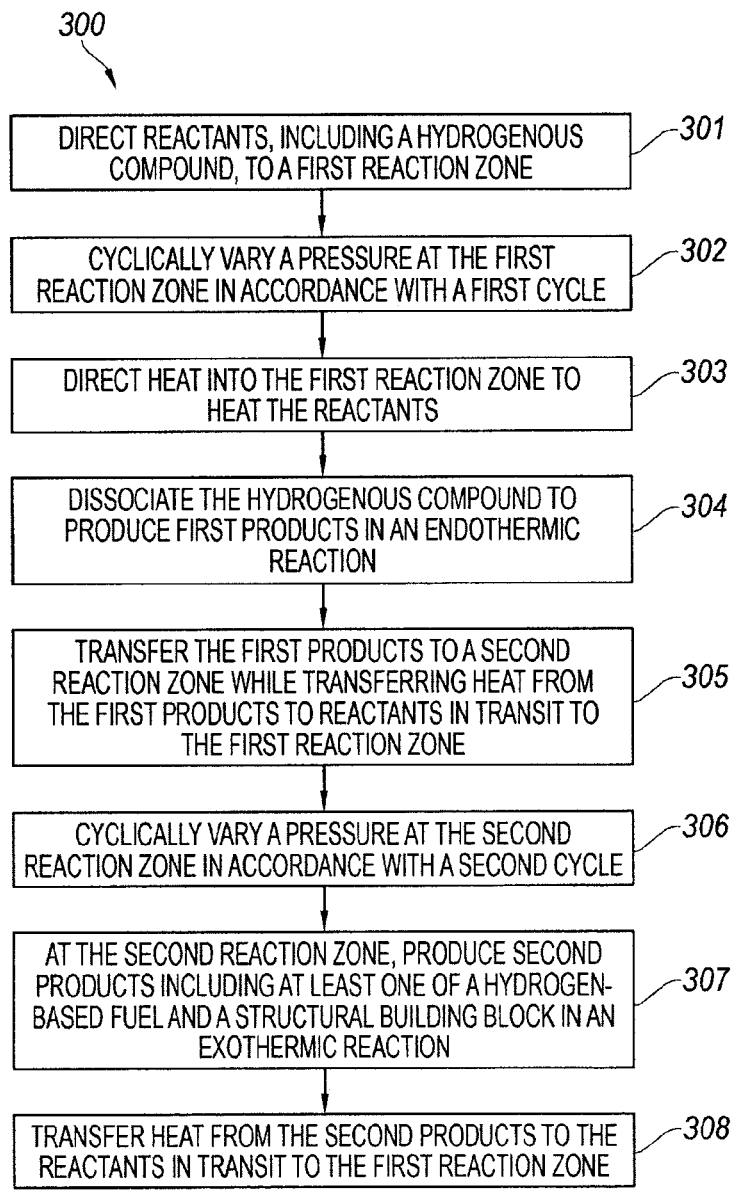
FIG. 3 is a flow diagram illustrating a chemical process having heat transfer characteristics and pressure variation characteristics in accordance with an embodiment of the present technology.

As noted above, Equation 1 represents an endothermic reaction, and Equation 2 represents an exothermic reaction. In addition, the forward progress of Equation 1 is supported by a relatively low pressure environment, while the forward progress of Equation 2 is supported by a relatively high pressure environment. The present technology includes controlling the heats and pressures produced and required in the two reaction zones in an inter-dependent manner to enhance (e.g. optimize) the production rate of methanol or other end products. FIG. 3 identifies the general manner in which this is accomplished, and the details of particular embodiments are then further described. Referring now to FIGS. 2 and 3, an overall process 300 that can be conducted with the system 100 described above includes directing reactants, including a hydrogenous compound, to a first reaction zone 110 (process portion 301). For example, the hydrogenous compound can include the methane described above. In other embodiments, the hydrogenous compound can include other hydrocarbons, or other hydrogen-bearing compounds that do not necessarily include carbon (e.g. nitrogenous compounds). In process portion 302, the pressure at the first reaction zone 110 is cyclically varied in accordance with a first cycle. For example, the pressure in the first reaction zone 110 can be adjusted by adjusting the pressure and/or flow rate with which reactants are directed into the first reaction zone 110, and by the rate at which the resulting products leave the first reaction zone 110. Process portion 303 includes directing heat into the first reaction zone to heat the reactants. The heat added to the first reaction zone 110 also increases the pressure in the first reaction zone 110 and accordingly represents an additional pressure control variable. Process portion 304 includes dissociating the hydrogenous compound to produce the first products in the endothermic reaction. In a representative embodiment, the endothermic reaction includes the reaction described above with reference to Equation 1, and in other embodiments, the reaction can include different products and/or reactants, while still absorbing heat.

In process portion 305, the first products are transferred to the second reaction zone 120, while transferring heat from the first products to reactants in transit to the first reaction zone 110. For example, the foregoing heat transfer process can be conducted by the first heat exchanger 140a described above with reference to FIG. 2. In process portion 306, the pressure at the second reaction zone 120 is cyclically varied in accordance with a second cycle. For example, the pressure in the second reaction zone 120 can be adjusted by adjusting the flow of first products into the second reaction zone 120, and by adjusting the flow of hydrogen (or another additional constituent) from the additional constituent source 154 into the second reaction zone 120. Process portion 307 includes producing second products at the second reaction zone 120, including at least one of a hydrogen-based fuel and a structural building block, in an exothermic reaction. For example, Equation 2 above includes forming methanol at the second reaction zone 120. In other embodiments, other processes can be conducted at the second reaction zone 120 to produce other hydrogen-based fuels. In still further embodiments, the resulting products can include structural building blocks, e.g., building blocks formed from carbon, boron, nitrogen, or other elements. Representative reactants, products and processes are described in further detail in the following co-pending U.S. Applications, filed Feb. 14, 2011 and incorporated herein by reference: application Ser. No. 13/027,208 titled "CHEMICAL PROCESSES AND REACTORS FOR EFFICIENTLY PRODUCING HYDROGEN FUELS AND STRUCTURAL MATERIALS, AND ASSOCIATED SYSTEMS AND METHODS"; application Ser. No. 13/027,068 titled "CARBON-BASED DURABLE GOODS AND RENEWABLE FUEL FROM BIOMASS WASTE DISSOCIATION"; and application Ser. No. 13/027,214 titled "ARCHITECTURAL CONSTRUCT HAVING FOR EXAMPLE A PLURALITY OF ARCHITECTURAL CRYSTALS". Process portion 308 includes transferring heat from the second products to the reactants in transit to the first reaction zone, e.g. via the second heat exchanger 140b described above with reference to FIG. 2.

The detailed steps outlined below identify the operation of the system 100 in accordance with a further particular embodiment:

1. Provide methane and carbon dioxide to the first reaction zone 110 under pressure. In a representative embodiment, the pressure in the first reaction zone 110 cycles between about 50 psi and about 1500 psi.
2. Elevate the temperature in the first reaction zone 110, causing an endothermic reaction to proceed.
3. Produce hydrogen and carbon monoxide (first products) at the first reaction zone 110. As the hydrogen and carbon monoxide are produced, the pressure in the first reaction zone 110 increases, which slows the reaction rate. As the reaction rate slows, the first reaction zone 110 continues to heat.
4. As the pressure in the first reaction zone 110 exceeds the pressure in the second reaction zone 120, direct the hydrogen and carbon monoxide to flow to second reaction zone 120. This will reduce the pressure in the first reaction zone 110.
5. As the carbon monoxide and hydrogen pass to the second reaction zone 120, transfer heat from these constituents to the methane and carbon dioxide flowing to the first reaction zone 110.
6. As the pressure decreases in the first reaction zone 110, the endothermic reaction rate there increases, as does the rate at which the hydrogen and carbon monoxide are delivered to the second reaction zone 120. This will increase the pressure in the second reaction zone 120.
7. Further pressurize the second reaction zone 120 with a separate source of hydrogen, e.g., provided in quantities that may exceed a stoichiometric balance.
8. The pressure in the second reaction zone 120 increases to the point that hydrogen and carbon monoxide from the first reaction zone 110 no longer enter the second reaction zone 120.
9. At the second reaction zone 120, combine carbon monoxide and hydrogen to produce methanol. The rate of this exothermic reaction increases with pressure.
10. Provide occasional release of the methanol from the second reaction zone 120, thus reducing the pressure there to reactivate the reaction bed. Releasing the pressure decreases the reaction rate. The pressure at the second reaction zone 120 can generally be at a higher pressure, but can accordingly cycle between a low valve of, e.g., about 50 psi, and a high valve of, e.g., about 5,000 psi or more.
11. Transfer heat from the methanol exiting the second reaction zone 120 to the methane and carbon dioxide flowing to the first reaction zone 110.
12. As the pressure in the second reaction zone 120 falls below the pressure in the first reaction zone 110, return to step 4.
13. Control the pressures in the first and second reaction zones 110, 120 to enhance (e.g., maximize) the production of methanol.

One feature of embodiments of the systems and processes described above with reference to FIG. 1-3 is that they include internally transferring heat between chemical constituents participating in the reactions. An advantage of this arrangement is that it reduces overall heat losses by recycling the heat produced and required in the exothermic and endothermic reactions, thus increasing the overall thermodynamic efficiency of the process. This in turn is expected to reduce the cost of producing high-quality, clean-burning hydrogen-based fuels and/or the building block constituents (e.g., carbon) that can be re-purposed to produce durable goods. Such goods represent an additional revenue stream that can in turn reduce the cost to produce the hydrogen-based fuel.

Another feature of at least some of the foregoing embodiments is that the pressures and flow rates of the constituents involved in the endothermic and exothermic reactions can be controlled to take advantage of reaction rates that are favored by high pressures and by low pressures. By coupling the flows of constituents in a manner that reflects the pressure differentials and temperature differentials between the reactions, the overall rate of production of the end product (e.g., methanol in a particular example) can be enhanced (e.g., optimized and/or maximized). This process can be performed automatically or autonomously by the controller 190 described above, based on sensed values throughout the system to provide real-time control of the product production.

From the foregoing, it will appreciated that specific embodiments of the technology have been described herein for purposes of illustration, but that various modifications may be made without deviating from the technology. For example, in addition to adjusting the foregoing parameters to efficiently utilize the available solar energy, the parameters can be adjusted to account for varying rates of solar energy, and/or to maximize the life of the catalysts in the first reaction zone 110 and/or the second reaction zone 120. While embodiments were discussed above in the context of a particular hydrocarbon (e.g., methane), other hydrocarbons (e.g., gasoline, propane, butane, diesel fuel, kerosene, bunker fuel and/or others) can also be suitable. In other embodiments, the reactants can include other carbon-based hydrogen donors, or hydrogen-containing compounds that include elements other than carbon. For example, the process can include extracting nitrogen from air or another source, and combining the nitrogen with hydrogen to produce ammonia. In still further embodiments, the system can operate without cyclically varying the pressure in the first and/or second reaction zones. For example, the first reaction zone can run at a relatively low pressure and the second reaction zone can run at a relatively high pressure. In such cases, a pump, piston or other device can add work to the first products to direct them to the second reaction zone. In a further aspect of such cases, ultrasonic energy at the first and/or second reaction zones can be used to load reactants and remove products.

A variety of sources can be used to produce suitable inputs for the reactor. For example, carbohydrates and carbon dioxide produced by breweries, bakeries, power plants, coking and/or calcining operations and/or others can be supplied to the reactor. In any of these embodiments, one feature of the processes is to increase the density of the hydrogen, for example, to the point where the hydrogen can be stored in existing fuel tanks currently used for conventional fuels.

Other suitable products that may be formed with carbon extracted during the foregoing processes can include diamond-like platings, e.g., for friction reduction, increased thermal conductivity and/or optical purposes, graphene crystal formation, macroscopic fibers, scrolls and other shapes, colorants and additives for polymers, and/or doped semiconductor materials.

Certain aspects of the technology described in the context of particular embodiments may be combined or eliminated in other embodiments. For example, multiple reactors of the type shown in FIG. 2 can produce different products that serve as reactants for each other. The specific details of the reactor described above in the context of FIG. 2, and the steps enumerated above can be eliminated or changed in other embodiments. Further, while advantages associated with certain embodiments of the technology have been described in the context of those embodiments, other embodiments may also exhibit such advantages, and not all embodiments need necessarily exhibit such advantages to fall within the scope of the present disclosure. Accordingly, the present disclosure and associated technology can encompass other embodiments not expressly shown or described herein.

To the extent not previously incorporated herein by reference, the present application incorporates by reference in their entirety the subject matter of each of the following materials: U.S. patent application Ser. No. 12/857,553, filed on Aug. 16, 2010 and titled SUSTAINABLE ECONOMIC DEVELOPMENT THROUGH INTEGRATED PRODUCTION OF RENEWABLE ENERGY, MATERIALS RESOURCES, AND NUTRIENT REGIMES; U.S. patent application Ser. No. 12/857,541, filed on Aug. 16, 2010 and titled SYSTEMS AND METHODS FOR SUSTAINABLE ECONOMIC DEVELOPMENT THROUGH INTEGRATED FULL SPECTRUM PRODUCTION OF RENEWABLE ENERGY; U.S. patent application Ser. No. 12/857,554, filed on Aug. 16, 2010 and titled SYSTEMS AND METHODS FOR SUSTAINABLE ECONOMIC DEVELOPMENT THROUGH INTEGRATED FULL SPECTRUM PRODUCTION OF RENEWABLE MATERIAL RESOURCES USING SOLAR THERMAL; U.S. patent application Ser. No. 12/857,502, filed on Aug. 16, 2010 and titled ENERGY SYSTEM FOR DWELLING SUPPORT; U.S. application Ser. No. 13/027,235, filed on Feb. 14, 2011, now U.S. Pat. No. 8,313,556 and titled DELIVERY SYSTEMS WITH IN-LINE SELECTIVE EXTRACTION DEVICES AND ASSOCIATED METHODS OF OPERATION; U.S. Patent Application No. 61/401,699, filed on Aug. 16, 2010 and titled COMPREHENSIVE COST MODELING OF AUTOGENOUS SYSTEMS AND PROCESSES FOR THE PRODUCTION OF ENERGY, MATERIAL RESOURCES AND NUTRIENT REGIMES; U.S. patent application Ser. No. 13/027,208, filed on Feb. 14, 2011, now U.S. Pat. No. 8,318,131 and titled CHEMICAL PROCESSES AND REACTORS FOR EFFICIENTLY PRODUCING HYDROGEN FUELS AND STRUCTURAL MATERIALS, AND ASSOCIATED SYSTEMS AND METHODS; U.S. patent application Ser. No. 13/026,996, filed on Feb. 14, 2011 and titled REACTOR VESSELS WITH TRANSMISSIVE SURFACES FOR PRODUCING HYDROGEN-BASED FUELS AND STRUCTURAL ELEMENTS, AND ASSOCIATED SYSTEMS AND METHODS; U.S. application Ser. No. 13/027,015, filed on Feb. 14, 2011 and titled CHEMICAL REACTORS WITH RE-RADIATING SURFACES AND ASSOCIATED SYSTEMS AND METHODS; U.S. application Ser. No. 13/027,244, filed on Feb. 14, 2011 and titled THERMAL TRANSFER DEVICE AND ASSOCIATED SYSTEMS AND METHODS; U.S. patent application Ser. No. 13/026,990, filed on Feb. 14, 2011, now U.S. Pat. No. 8,187,549 and titled CHEMICAL REACTORS WITH ANNULARLY POSITIONED DELIVERY AND REMOVAL DEVICES, AND ASSOCIATED SYSTEMS AND METHODS; U.S. application Ser. No. 13/027,181, filed on Feb. 14, 2011, now U.S. Pat. No. 8,187,550 and titled REACTORS FOR CONDUCTING THERMOCHEMICAL PROCESSES WITH SOLAR HEAT INPUT, AND ASSOCIATED SYSTEMS AND METHODS; U.S. application Ser. No. 13/027,215, filed on Feb. 14, 2011, now U.S. Pat. No. 8,318,269 and titled INDUCTION FOR THERMOCHEMICAL PROCESS, AND ASSOCIATED SYSTEMS AND METHODS; U.S. application Ser. No. 13/027,198, filed on Feb. 14, 2011 and titled COUPLED THERMOCHEMICAL REACTORS AND ENGINES, AND ASSOCIATED SYSTEMS AND METHODS; U.S. Patent Application No. 61/385,508, filed on Sep. 22, 2010 and, titled REDUCING AND HARVESTING DRAG ENERGY ON MOBILE ENGINES USING THERMAL CHEMICAL REGENERATION; U.S. application Ser. No. 13/027,214, filed on Feb. 14, 2011 and titled ARCHITECTURAL CONSTRUCT HAVING FOR EXAMPLE A PLURALITY OF ARCHITECTURAL CRYSTALS; U.S. patent application Ser. No. 12/806,634, filed on Aug. 16, 2010 and titled METHODS AND APPARATUSES FOR DETECTION OF PROPERTIES OF FLUID CONVEYANCE SYSTEMS; U.S. application Ser. No. 13/027,188, filed on Feb. 14, 2011, now U.S. Pat. No. 8,312,759 and titled METHODS, DEVICES, AND SYSTEMS FOR DETECTING PROPERTIES OF TARGET SAMPLES; U.S. patent application Ser. No. 13/027,068, filed on Feb. 14, 2011, now U.S. Pat. No. 8,318,997 and titled SYSTEM FOR PROCESSING BIOMASS INTO HYDROCARBONS, ALCOHOL VAPORS, HYDROGEN, CARBON, ETC.; U.S. application Ser. No. 13/027,196, filed on Feb. 14, 2011 and titled CARBON RECYCLING AND REINVESTMENT USING THERMOCHEMICAL REGENERATION; U.S. patent application Ser. No. 13/027,195, filed on Feb. 14, 2011, now U.S. Pat. No. 8,784,095 and titled OXYGENATED FUEL; U.S. Patent Application No. 61/237,419, filed on Aug. 27, 2009 and titled CARBON SEQUESTRATION; U.S. Patent Application No. 61/237,425, filed on Aug. 27, 2009 and titled OXYGENATED FUEL PRODUCTION; U.S. patent application Ser. No. 13/027,197, filed on Feb. 14, 2011, now U.S. Pat. No. 8,070,835 and titled MULTI-PURPOSE RENEWABLE FUEL FOR ISOLATING CONTAMINANTS AND STORING ENERGY; U.S. Patent Application No. 61/421,189, filed on Dec. 8, 2010 and titled LIQUID FUELS FROM HYDROGEN, OXIDES OF CARBON, AND/OR NITROGEN; AND PRODUCTION OF CARBON FOR MANUFACTURING DURABLE GOODS; and U.S. application Ser. No. 13/027,185, filed on Feb. 14, 2011, now U.S. Pat. No. 8,328,888 and titled ENGINEERED FUEL STORAGE, RESPECIATION AND TRANSPORT.

I claim:
1. A chemical reactor system, comprising:
  a first reaction zone and a heat path positioned to direct primary heat into the first reaction zone;
  a reactant source coupled to the first reaction zone;
  a second reaction zone in fluid communication with the first reaction zone;
  a secondary heat source coupled to the first reaction zone;
  a solar input sensor;
  a flow rate control mechanism coupled between the first and second reaction zones for controlling a flow rate between the first and second reaction zones; and a controller programmed with cyclical pressurization instructions that, when executed:
cyclically pressurize the first reaction zone;
cyclically pressurize the second reaction zone in a manner that depends at least in part on a flow of a product from the first reaction zone to the second reaction zone; and
actuate the secondary heat source in response to an input from the solar input sensor corresponding to low solar input to the first reaction zone.

2. The system of claim 1, further comprising:
a first heat exchanger positioned to direct heat from a first product leaving the first reaction zone to a reactant entering the first reaction zone;
a second heat exchanger positioned to direct heat from a second product leaving the second reaction zone to the reactant entering the first reaction zone.

3. The system of claim 2 wherein:
the first heat exchanger is positioned in fluid communication with the first and second reaction zones and has:
a first flow path positioned to direct products from the first reaction zone into the second reaction zone; and
a second flow path in thermal communication with the first flow path and coupled between the reactant source and the first reaction zone; and wherein
the second heat exchanger is positioned in fluid communication with the second reaction zone and has:
a third flow path positioned to direct products from the second reactor; and
a fourth flow path in thermal communication with the second flow path and coupled between the reactant source and the first reaction zone.

4. The system of claim 1 wherein the controller is programmed with cyclical pressurization instructions that, when executed:
direct a first actuator to cyclically pressurize the first reaction zone; and
direct a second actuator to cyclically pressurize the first second reaction zone in a manner that is correlated with pressurization of the first reaction zone.

5. The system of claim 1 wherein the heat path includes a reactor surface transmissive to solar energy, and wherein the system further comprises a solar collector positioned to direct solar radiation through the reactor surface.

6. The system of claim 1 wherein the mechanism includes a check valve positioned to admit the first product into the second reaction zone when the pressure in the first reaction zone is greater than the pressure in the second reaction zone, and prevent fluid communication between the first and second reaction zones when the pressure in the second reaction zone is greater than the pressure in the first reaction zone.

7. The system of claim 1 wherein the controller is programmed with cyclical pressurization instructions that cyclically pressurize the first reaction zone by directing pressurized reactant into the first reaction zone.

8. A chemical reactor system, comprising:
a cylindrical housing having a longitudinal axis;
a first reaction zone and a heat path positioned to direct primary heat into the first reaction zone, the first reaction zone being housed within the cylindrical housing;
a reactant source coupled to the first reaction zone;
a second reaction zone in fluid communication with the first reaction zone and housed within the cylindrical housing;
a concave solar collector actuatable to direct solar energy to the first reaction zone or the second reaction zone;
a flow rate control mechanism coupled between the first and second reaction zones to control a flow rate between the first and second reaction zones; and
a controller operatively coupled to the flow rate control mechanism, the controller being programmed with cyclical pressurization instructions that, when executed:
cyclically pressurize the first reaction zone;
cyclically pressurize the second reaction zone in a manner that depends at least in part on a flow of a product from the first reaction zone to the second reaction zone.

9. The chemical reactor system of claim 8, wherein the first reaction zone and the second reaction zone are aligned along the longitudinal axis of the cylindrical housing.

10. The chemical reactor system of claim 8, wherein the concave solar collector is positionable along the longitudinal axis of the cylindrical housing.

* * * * *